(12) United States Patent
Meudt et al.

(10) Patent No.: US 7,939,688 B2
(45) Date of Patent: May 10, 2011

(54) PROCESS FOR PREPARING NITRILES BY ELIMINATION REACTIONS

(75) Inventors: Andreas Meudt, Hofheim (DE); Sven Nerdinger, Kiefersfelden (DE); Claudius Boehm, Frankfurt am Main (DE)

(73) Assignee: Archimica GmbH, Frankfurt am Main (DE)

( * ) Notice: Subject to any disclaimer, the term of this patent is extended or adjusted under 35 U.S.C. 154(b) by 510 days.

(21) Appl. No.: 11/996,105

(22) PCT Filed: Jul. 5, 2006

(86) PCT No.: PCT/EP2006/006548
§ 371 (c)(1),
(2), (4) Date: Jan. 18, 2008

(87) PCT Pub. No.: WO2007/012387
PCT Pub. Date: Feb. 1, 2007

(65) Prior Publication Data
US 2008/0242884 A1    Oct. 2, 2008

(30) Foreign Application Priority Data

Jul. 25, 2005  (DE) .......................... 10 2005 035 250

(51) Int. Cl.
*C07C 253/20*    (2006.01)
(52) U.S. Cl. ...................................................... 558/312
(58) Field of Classification Search ................ 558/312
See application file for complete search history.

(56) References Cited

U.S. PATENT DOCUMENTS

2007/0161813  A1*  7/2007  Meudt et al. .................. 558/382

FOREIGN PATENT DOCUMENTS

| DE | 100 63 493 A1 | | 6/2002 |
|---|---|---|---|
| WO | WO 99/37611 A1 | | 7/1999 |
| WO | WO 2005/070879 | * | 8/2005 |
| WO | WO 2005070879 | | 8/2005 |

OTHER PUBLICATIONS

Clariant Inc. "T3P The water scavenger" 2005, pp. 1-12.*
J. Glauder, "T3P: Propane phosphonic acid anhydride for peptid & amide synthesis", Internet Citation, Mar. 2004, XP002403967; http://www.archemica.com/images/Library_Files/030004CPHASpecChemT3PTechArticle.pdf.
Anonym., "T3P: The Water Scavenger. T3P (Propane Phosphonic Acid Anhydride)—A Versatile Condensation Reagent", Internet Citation, Jun. 1999, XP002337773; http://www.lse.clariant.com/lse/e2wtools.nsf/lookupDownloads/T3Pnew.pdf/$FILE/T3Pnew.pdf.
J. March et al.; "Advanced Organic Chemistry, Second Edition" McGraw-Hill, US, 1977, pp. 953-954.

* cited by examiner

*Primary Examiner* — Joseph R Kosack
(74) *Attorney, Agent, or Firm* — ProPat, L.L.C.

(57) ABSTRACT

Process for preparing nitriles by reacting N-alkylcarboxamides ($RCO-NHR^1$) or ammonium salts of carboxylic acids ($RCOO-NH_3R^{1+}$) or carboxylic acids in the presence of alkylamines or ammonium salts ($RCOOH+NH^2R^1$, $RCOOH+NH_3R^{1+}$), respectively, R being an arbitrarily substituted linear or branched $C_1-C_{12}$-alkyl radical, a $C_3-C_{12}$ cycloalkyl radical or an alkenyl, alkynyl or aryl or heteroaryl radical and $R^1$ being an arbitrary substituted, linear or branched $C_2-C_1$ alkyl radical, a $C_3-C_{12}$ cycloalkyl radical or an alkenyl or alkynyl radical, with phosphonic anhydrides in the presence of an optional base in an organic solvent at a temperature in the range from –30 to 180° C. In advantageous embodiments, the phosphonic anhydride is a 2,4,6-substituted 1,3,5,2,4,6-trioxatriphosphinane 2,4,6-trioxide of the formula (I)

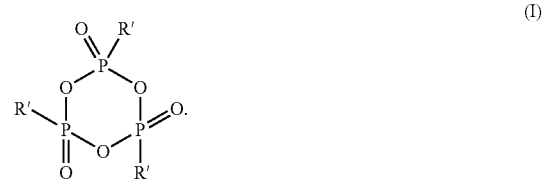

(I)

9 Claims, No Drawings

PROCESS FOR PREPARING NITRILES BY ELIMINATION REACTIONS

CROSS-REFERENCE TO RELATED APPLICATIONS

This application is being filed under Rule 1.371 as a National Stage Application of pending International Application No. PCT/EP2006/006548 filed Jul. 5, 2006, which claims priority to the following parent application: German Patent Application No. 10 2005 035 250.2, filed Jul. 25, 2005. Both International Application No. PCT/EP2006/006548 and German Patent Application No. 10 2005 035 250.2 are hereby incorporated by reference herein in their entirety.

FIELD OF THE INVENTION

The present invention relates to processes for preparing nitriles by elimination reactions. The present invention more particularly relates to processes for preparing nitrites by reacting phosphonic anhydrides with N-alkylcarboxamides or ammonium salts of carboxylic acids or carboxylic acids in the presence of alkylamines or ammonium salts.

BACKGROUND OF THE INVENTION

Nitriles are important intermediates that have extremely diverse uses in organic synthesis. Both compound classes exhibit high reactivity of the C,N multiple bond, as a result of which countless heterocarbonyl reactions are made possible. The significance in modern organic synthesis is restricted only by limitations of accessibility of these compound classes. Standard processes for preparing nitrites are dehydrations of carboxamides, where countless reagents, such as, for example, POCl3 can be used.

In modern organic synthesis, the importance of chemoselective, regioselective and stereoselective reagents is increasing explosively. If, for example, it is desired, in a complex molecule with numerous functional groups, some of which only have slight reactivity differences, to convert a certain acid group into an amide without influencing other groups (e.g. epimerization of chiral functionalities), it is no longer possible to use unselective methods such as $SOCl_2$. A highly selective reagent for the extremely selective amide bond linkage, which produces excellent selectivities and yields without epimerization even in oligopeptides, is propanephosphonic anhydride (T3P®). This reagent is commercially available in various solvents and is easy to use. The performance of this reagent is so high that the problem of linking amide and peptide bonds in complex molecules can nowadays be considered solved.

A comparable solution for converting carboxylic acids and N-alkylcarboxamides into the corresponding nitriles has hitherto been lacking. Although the known reagents can bring about the desired transformations, other groups are often likewise influenced in the process. In many cases, even distant stereocenters are epimerized as a result of the drastic conditions required.

It would therefore be very desirable to have a process which can convert carboxylic acids and N-alkyl-carboxamides into the corresponding nitriles by dehydration, but which at the same time has very high chemoselectivities, and can additionally be used in economically feasible processes. The known reagents do not solve this problem as will be demonstrated by a few examples: although POCl3 in combination with bases can bring about the specified reactions, almost every possible functional group likewise reacts with this reagent. Using dicyclohexylcarbodiimide (DCC), it is likewise possible to carry out the desired transformation to nitriles, although partial epimerizations often occur in the process; even worse, however, are often the properties of the dicyclo-hexylurea formed as by-product, which can often only be separated from the product with difficulty, and then only by chromatographic separations. The use of water-soluble DCC derivatives is in most cases not economically feasible due to their very high cost and difficult accessibility.

SUMMARY OF ADVANTAGEOUS EMBODIMENTS OF THE INVENTION

Surprisingly, it has been found that alkylphosphonic anhydrides all solve these problems and are ideal and highly selective reagents for converting carboxylic acids and N-alkylcarboxamides by dehydration into the corresponding nitriles, where at the same time the desired freedom from epimerization and maximum regioselectivity and stereoselectivity are observed.

DETAILED DESCRIPTION OF ADVANTAGEOUS EMBODIMENTS OF THE INVENTION

The present invention thus relates to a highly selective process for preparing nitriles of the formula (II),

$$R—C≡N \quad (II)$$

by reacting
N-alkylcarboxamides. ($RCO—NHR^1$) or
ammonium salts of carboxylic acids ($RCOO—NH_3R^{1+}$) or
carboxylic acids in the presence of alkylamines or ammonium salts ($RCOOH+NH_2R^1$, $RCOOH+NH_3R^{1+}$)
where R is an arbitrarily substituted linear or branched $C_1$-$C_{12}$-alkyl radical, a $C_3$-$C_{12}$-cycloalkyl radical, alkenyl radical, alkynyl radical or an aryl radical or heteroaryl radical and $R^1$ is an arbitrarily substituted, linear or branched, $C_2$-$C_{12}$-alkyl radical, a $C_3$-$C_{12}$-cycloalkyl radical, alkenyl radical, alkynyl radical,
with phosphonic anhydrides optionally in the presence of a base in an organic solvent at a temperature in the range from −30 to 180° C.

In a preferred embodiment according to the invention, the phosphonic anhydride is a 2,4,6-substituted 1,3,5,2,4,6-trioxatriphosphinane 2,4,6-trioxide of the formula (I),

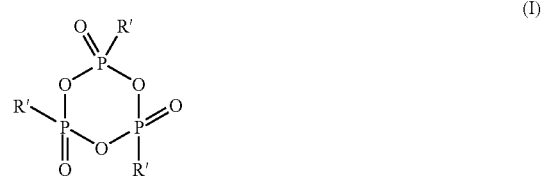

(I)

R', independently of one another, are open-chain or branched, saturated or unsaturated, straight-chain $C_1$ to $C_{16}$-alkyl radicals, in particular a $C_2$ to $C_{12}$-alkyl radical, or cyclic $C_3$ to $C_{16}$-alkyl radicals or aryl or heteroaryl. Particular preference is given to phosphonic anhydrides of the formula (I) in which R' is a methyl, ethyl, n-propyl, isopropyl, n-butyl, 2-butyl, isobutyl, pentyl, hexyl, in particular an ethyl radical, propyl radical and/or butyl radical, very particularly preferably propanephosphonic anhydride (T3P® anhydride from Archimica, Frankfurt am Main, Germany).

The dehydration to give nitriles (II) is carried out here generally at temperatures in the range from −30 to −180° C., preference being given to temperatures in the range from 0 to 120° C., in particular +30 to +70° C., where lower temperatures are generally correlated with higher selectivities. The reaction time is dependent on the temperature used and is generally 1 to 12 hours, in particular 3 to 6 hours.

The phosphonic anhydride can be added to the reaction medium either in the form of a melt or in the form of a liquid mixture dissolved in a solvent. Suitable solvents here are those which do not undergo secondary reactions with the phosphonic anhydride, these are all aprotic organic solvents, such as, for example, ligroin, butane, pentane, hexane, heptane, octane, cyclopentane, cyclohexane, cycloheptane, cyclooctane, dichloromethane, chloroform, tetrachloromethane, 1,2-dichloroethane, 1,1,2,2-tetrachloroethane, methyl acetate, ethyl acetate, propyl acetate, butyl acetate, dimethylformamide, diethylformamide, dimethylacetamide, diethylacetamide, diethyl ether, diisopropyl ether, tert-butyl methyl ether, THF, dioxane, acetonitrile or mixtures of these, particularly preferably dichloromethane, chloroform, ethyl acetate, propyl acetate, butyl acetate, dimethylformamide, diethylformamide, dimethylacetamide, (diethylacetamide, diisopropyl ether, tert-butyl methyl ether, THF, dioxane, acetonitrile or mixtures off these, very particularly preferably dichloromethane, chloroform, ethyl acetate, butyl acetate, dimethylformamide, dimethylacetamide, tert-butyl methyl ether, THF, dioxane, acetonitrile or mixtures of these, especially preferably THF, ethyl acetate, or butyl acetate.

The addition of the phosphonic anhydride takes place at least stoichiometrically based on the starting compound (carboxylic acid), but can also be superstoichiometric, for example in the ratio 2:1.

The reactions are preferably carried out by initially introducing the corresponding N-alkylamide in a solvent, then heating to the reaction temperature and then, through metered addition of the phosphoric anhydride as melt or solution in one of the abovementioned solvents, said N-alkylamide is converted to the desired nitrile.

The reaction product is preferably isolated by hydrolysis and simple phase separation since the by-products of the phosphonic anhydrides are generally very readily water-soluble. Depending on the nature of the product to be isolated, after-extractions may also be required here. The phosphonic anhydride by-product formed does not often disrupt secondary reactions, meaning that even direct use of the resulting reaction solutions often affords very good results.

In a further preferred embodiment, an ammonium salt of a carboxylic acid ($RCOO-NH_3R^{1+}$) is converted to a nitrile through simple heating with the phosphonic anhydride analogously to the process described above. This also gives rise to a very elegant and likewise extremely selective process for directly converting carboxylic acids into nitrites in such a way that any desired ammonium salt is added to the carboxylic acid and then it is reacted with a phosphonic anhydride in the presence of a base.

Suitable bases are, for example, tertiary amines, such as triethylamine, tripropylamine, benzyldimethylamine, N,N-dimethylaniline or pyridine. The base is usually added in a ratio of from 1 to 5 equivalents, preferably 1 to 3, in particular 1 to 27 equivalents, based on the carboxylic acid.

The process can also be carried out by admixing a solution or suspension of the carboxylic acid to be converted in hydrocarbons or esters such as ethyl acetate or butyl acetate with at least one equivalent of N-alkylamine and then treating it with the phosphonic anhydride.

All of the specified procedures are characterized by very good yields (typically 90-100%, in particular >95%) and simple work-up, coupled with the absence of secondary reactions and of epimerizations. The selectivities and the product purities of the reaction according to the invention are in the range from 97-100%, in particular 99-100%.

The process according to the invention will the illustrated by the examples below, without limiting the invention thereto:

Example 1

Benzonitrile from Benzoic Acid 1 mol of benzoic acid, 1.1 mol of tert-butylamine and 2 mol of $NEt_3$ are initially introduced into 150 ml of ethyl acetate. 1.2 mol of T3P® propanephosphonic anhydride solution in ethyl acetate (50% w/w) are metered in over the course of one hour, then the mixture is afterstirred for a further three hours at this temperature. At this time, the reaction GC indicated a conversion of 100%. The reaction mixture is heated to boiling for 3 hours and, after cooling to room temperature, 180 ml of water were added and the phases were separated. The organic phase was distilled. The isolated yield of this reaction was 96%, HPLC purity 98% (a/a).

Example 2

4-Methoxybenzonitrile from N-tert-octyl-4-methoxybenzamide 1 mol of N-tert-octyl-4-methoxybenzamide and 2 mol of $NEt_3$ are initially introduced into 150 ml of ethyl acetate. 1.2 mol of T3P® propanephosphonic anhydride solution in ethyl acetate (50% w/w) are metered in. The reaction mixture is heated to boiling for 3 hours and, after cooling to room temperature, 180 ml of water were added and the phases were separated. The organic phase was distilled. The isolated yield of this reaction was 96%, HPLC purity 98% (a/a).

Example 3

Terephthalodinitrile from N-tert-octyl-4-cyanobenzamide 1 mol of N-tert-octyl-4-cyanobenzamide and 2 mol of $NEt_3$ are initially introduced into 150 ml of ethyl acetate. 1.2 mol of T3P® propanephosphonic anhydride solution in ethyl acetate (50% w/w) are metered in. The reaction mixture is heated to boiling for 3 hours and, after cooling to room temperature, 180 ml of water were added and the phases were separated. The organic phase was distilled. The isolated yield of this reaction was 95%, HPLC purity 97% (a/a).

Example 4

4-Bromo-3,5-dimethoxybenzonitrile from N-tert-octyl-4-bromo-3,5-dimethoxybenzamide 1 mol of N-tert-octyl-4-bromo-3,5-dimethoxybenzamide and 2 mol of $NEt_3$ are initially introduced into 150 ml of ethyl acetate. 1.2 mol of T3P® propanephosphonic anhydride solution in ethyl acetate (50% w/w) are metered in. The reaction mixture is heated to boiling for 3 hours and, after cooling to room temperature, 180 ml of water were added and the phases were separated. The organic phase was distilled. The isolated yield of this reaction was 95%, HPLC purity 97% (a/a).

The invention claimed is:

1. A process for preparing nitriles of the formula (II)

$$R-C\equiv N \qquad (II)$$

comprising reacting a reaction solution comprising
N-alkylcarboxamides of the formula RCO—NHR$^1$ or
ammonium salts of carboxylic acids of the formula RCOO$^-$NH$_3$R$^{1+}$ or
carboxylic acids in the presence of alkylamines or ammonium salts of the formulae

RCOOH+NH$_2$R$^1$,RCOOH+NH$_3$R$^{1+}$ where
R is an arbitrarily substituted linear or branched $C_1$-$C_{12}$-alkyl radical, a $C_3$-$C_{12}$ cycloalkyl radical, alkenyl radical, alkynyl radical or an aryl radical or heteroaryl radical and
R$^1$ is an arbitrarily substituted, linear or branched, $C_2$-$C_{12}$-alkyl radical, a $C_3$-$C_{12}$-cycloalkyl radical, alkenyl radical, alkynyl radical, with phosphonic anhydrides in the presence or absence of a base in an organic solvent at a reaction temperature in the range from −30 to 180° C., wherein the phosphonic anhydride is propanephosphonic anhydride.

2. The process as claimed in claim 1, wherein the phosphonic anhydride is added either in the form of a melt or dissolved in a solvent of the amide- or formamide-containing reaction solution.

3. The process as claimed in claim 2, wherein the phosphonic anhydride is added in an aprotic solvent.

4. The process as claimed in claim 2, wherein the phosphonic anhydride is added in an aprotic solvent in a ratio of 1:1 to 2:1, based on the carboxylic acid.

5. The process as claimed in claim 1, wherein the base is present and the base is a tertiary amine.

6. The process as claimed in claim 5, wherein the tertiary amine is triethylamine, tripropylamine, benzyldimethylamine, N,N-dimethylaniline or pyridine.

7. The process as claimed in claim 1, wherein the base is present and is added in a ratio of from 1 to 2 equivalents, based on the carboxylic acid.

8. The process as claimed in claim 1, wherein the base is present and is added in a ratio of from 1 to 1.2 equivalents, based on the carboxylic acid.

9. The process as claimed in claim 1, said process further comprising heating the reaction solution to the reaction temperature after the phosphoric anhydride has been added.

* * * * *